United States Patent [19]

Sauerbier et al.

[11] Patent Number: 5,262,169
[45] Date of Patent: Nov. 16, 1993

[54] TABLETS AND GRANULATES CONTAINING MESNA AS ACTIVE SUBSTANCE

[75] Inventors: Dieter Sauerbier, Werter; Jürgen Engel, Alzenau; Eckhard Milsmann, Bielefeld, all of Fed. Rep. of Germany

[73] Assignee: Asta Medica Aktiengesellschaft, Fed. Rep. of Germany

[21] Appl. No.: 730,178

[22] Filed: Jul. 16, 1991

[30] Foreign Application Priority Data

Jul. 16, 1990 [DE] Fed. Rep. of Germany ....... 4022525

[51] Int. Cl.$^5$ .............. A61K 9/16; A61K 9/20; A61K 9/28; A61K 31/185
[52] U.S. Cl. .................... 424/465; 424/464; 424/469; 424/470; 424/474; 424/475; 424/489; 514/578; 514/772.3; 514/774; 514/778; 514/781; 514/784; 514/770; 514/777
[58] Field of Search .............. 424/464, 465, 466, 489; 514/578

[56] References Cited

U.S. PATENT DOCUMENTS

| | | | |
|---|---|---|---|
| 4,734,418 | 3/1988 | Yokoyama et al. | 514/215 |
| 4,959,215 | 9/1990 | Sauerbier et al. | 424/422 |
| 5,019,596 | 5/1991 | Reiner et al. | 514/578 |

FOREIGN PATENT DOCUMENTS 0198542 4/1986 European Pat. Off. .

Primary Examiner—Thurman K. Page
Assistant Examiner—James M. Spear
Attorney, Agent, or Firm—Cushman, Darby & Cushman

[57] ABSTRACT

A granulate containing mesna is made by granulating mesna in the presence of an alcohol, acetone or a mixture of one of these with water. The granulate may be converted to tablets, along with other agents. The tablets contain:

0.01–1 parts by weight of a binding agent
0.03–0.4 parts by weight of a disintegrant
0.01–0.2 parts by weight of a lubricant and
0.1–1 parts by weight of a filling agent as well as, in the case of an effervescent tablet, an additional 0.05–30 parts by weight of a conventional physiologically acceptable effervescent mixture.

17 Claims, No Drawings

TABLETS AND GRANULATES CONTAINING MESNA AS ACTIVE SUBSTANCE

The present invention relates to oral dosage forms of mesna.

BACKGROUND OF THE INVENTION

The chemical name of the active substance mesna is sodium 2-mercaptoethanesulfonate.

Mesna is useful, for example, to protect urinary organs when ifosfamide is used to treat tumors. Mesna has also been used for a long time as a mucolytic agent.

Mesna is a white hygroscopic powder with a characteristic odor. The substance is very sensitive to oxidation and rapidly decomposes to dimesna on contact with oxygen, particularly in a humid atmosphere.

Mesna has hitherto been administered orally, parenterally and as an inhalation. All the dosage forms which have been used in the past have been liquid formulations. For example, the only oral dosage form which has been available has been an aqueous solution. Since mesna is very sensitive to oxidation and reacts in the presence of oxygen to dimesna, which is poorly absorbed, the aqueous solution must be protected against oxygen. For this reason the solution is sealed in glass ampoules The ampoule has to be opened by the patient just before use. This is a complicated procedure for oral use. What is more, the solution is relatively heavy and needs a great deal of storage space.

The major disadvantage of the orally-administered solution is its very unpleasant taste, with the result that patients are very reluctant to take it, even when flavored. Since patients being treated with cytostatic agents very often tend to suffer from nausea and lack of appetite, the poor taste further impairs compliance. The reasons set out above explain the long-standing need for an agreeable-tasting, stable and individually dosable oral form of administration.

Although mesna is a crystalline powder, all attempts at manufacturing tablets, coated tablets or soft gelatin capsules have hitherto failed. In the case of soft gelatin capsules, embedding mesna in a lipid matrix provided good protection against oxygen and decomposition. Interaction between mesna and the capsule shell, however, repeatedly resulted in the capsules splitting during storage: the capsules were physically unstable Direct tabletting of the active substance was also unsuccessful because of the high bulk volume of up to 500 ml/100g.

It was not possible to achieve aqueous granulation of mesna to prepare for tabletting either using conventional pasting or by means of fluidized air bed granulation, since mesna liquefies immediately on contact with water.

SUMMARY OF THE INVENTION

In accordance with the present invention, it has now surprisingly been found that mesna lends itself well to granulation with isopropanol or a mixture of water and isopropanol, and that the granulate obtained can be effectively further processed into tablets and film-coated tablets using additional auxiliary substances. These tablets display good chemical stability, are easy to administer, and are virtually tasteless if swallowed immediately.

Therefore, the present invention provides a tablet which, related to one part by weight of mesna, contains
0.01–1 parts by weight of a binding agent
0.03–0.4 parts by weight of a disintegrant
0 01–0.2 parts by weight of a lubricant and
0.1–1 parts by weight of a filling agent
as well as, in the case of an effervescent tablet, an additional 0.05–30 parts by weight of a conventional physiologically acceptable effervescent mixture. A tablet of this kind may also optionally contain conventional physiologically acceptable flavoring, sweetening and/or aromatizing substances.

The invention also relates to a granulate that may be used for manufacturing a tablet of the kind just described.

The proportion by weight of mesna in a tablet of this kind generally comprises between 10 and 80 percent by weight, the remainder being the previously-mentioned auxiliary substances, the amount of which is in each case related to one part by weight of mesna. The formulations of the invention contain for example 100 mg to 800 mg of mesna, preferably 300 mg to 500 mg of mesna.

The invention also provides a process for the preparation of mesna tablets of the kind described above which contain, as active ingredient, mesna (for example 10–80% by weight), optionally conventional flavoring, sweetening and aromatizing substances as well as, related in each case to one part by weight of mesna:
0.01–1 parts by weight of a binding agent
0.03–0.4 parts by weight of a disintegrant
0.01–0.2 parts by weight of a lubricant
0.1–1 parts by weight of a filling agent
as well as, in the case of an effervescent tablet, an additional 0.05–30 parts by weight of a conventional physiologically acceptable effervescent mixture. The invention also provides for the manufacture of an appropriate granulate from which such tablets can be made. In accordance with the invention, mesna is first granulated in a manner known per se with at least one member of the group consisting of a $C_1$–$C_4$-alcohol and acetone or a mixture of one or more of these cited organic agents with water, and a filling agent as well as binding agents, optionally also a disintegrant. The above-mentioned auxiliary substances may be used in the amounts mentioned above. Alternatively, only a portion of those amounts may be added, the remainder being added after granulation. The granulate obtained is dried and then the lubricant and, optionally, the remaining binding and filling agents and disintegrant are added. The entire volume is then homogenized and pressed into tablets. Optionally, the tablets so-obtained are provided with a film coating in conventional manner. In the case of an effervescent tablet, the organic acid of the effervescent mixture or also the entire effervescent mixture is also added after the granulate has been dried.

Examples of the auxiliary and carrier substances of the invention according to the claims are:

| | |
|---|---|
| Filling agents: | for example starch, cellulose, lactose, saccharose, fructose, sorbitol, mannitol, calcium phosphate, calcium hydrogen phosphate. The entire amount of filling agent in the tablet may be 5–95% by weight. |
| Binding agents: | for example gelatin, cellulose ethers, pectins, alginates (sodium alginate), polyvinyl pyrrolidone, lactose, microcrystalline cellulose (Avicel). The entire amount of binding agents in the tablets may be 0.1–80% by weight. |
| Disintegrants: | for example alginates, starch (corn |

| | |
|---|---|
| | starch), pectins, carboxymethyl cellulose, ultramyl pectin, bentonite, polyvinyl polypyrrolidone (in the case of polyvinyl polypyrrolidone the filamentary macromolecules of the polyvinyl pyrrolidone are cross-linked; the product is insoluble in all conventional solvents; it has a porous structure and has great swelling capacity); grain distribution: ca. 50% > 50 µm, maximum 1% > 250 µm; bulk density: 280-380 g/liter The entire amount of disintegrant in the tablet may be 1-10% by weight. |
| Lubricants: | for example stearic acid, stearates, polyglycols, talcum, highly disperse silicon dioxide. The amount of lubricant for each part by weight of mesna is, in the case of a conventional tablet which is intended to be swallowed, preferably 0.01-0.1, in particular 0.01-0.05 parts by weight. In the case of an effervescent tablet, 0.05-0.15 parts by weight of lubricant are preferably used for each part by weight of mesna. The entire amount of lubricant in the tablet may be 0.2-10% by weight. |

Lactose (for example coarse-grained) and/or calcium hydrogen phosphate is preferably used as filling agent; polyvinyl pyrrolidone and/or microcrystalline cellulose (Avicel) as binding agent; starch, preferably corn starch as disintegrant, and stearates (for example magnesium stearate) as lubricant.

With 1 part by weight of mesna it is, for example, possible to use:

lactose 0.06-0.4 parts by weight, preferably 0.13-0.33, in particular 0.2-0.25 parts by weight.

Calcium hydrogen phosphate 0.03-0.3 parts by weight, preferably 0.05-0.23, in particular 0.08-0.12 parts by weight.

Corn starch (for the granulate phase) 0.03-0.3 parts by weight, preferably 0.13-0.33, in particular 0.2-0.25 parts by weight.

Polyvinyl pyrrolidone 0.02-0.1 parts by weight, preferably 0.03-0.06, in particular 0.04-0.06 parts by weight.

Microcrystalline cellulose (Avicel) 0.03-0.3 parts by weight, preferably 0.05-0.25, in particular 0.08-0.1 parts by weight.

Corn starch (for the outer phase, that is, after granulation) 0.02-0.25 parts by weight, preferably 0.03-0.1, in particular 0.06-0.07 parts by weight.

Magnesium stearate 0.003-0.03 parts by weight, preferably 0.01-0.02, in particular 0.015-0.018 parts by weight.

The ratio of the auxiliary substances amongst themselves is for example in the range:
Lactose:tricalcium phosphate:corn starch:polyvinyl pyrrolidone (granulate phase):Avicel:corn starch:magnesium stearate (outer phase) —1:0.4:0.4:0.2:0.4:0.3: 0.07.

If binding agents other than polyvinyl pyrrolidone are used, it is for example possible to use the following amounts for each part by weight of mesna:

| | |
|---|---|
| gelatin | 0.01-0.06 parts to one part by weight mesna |
| cellulose ether | 0.005-0.04 parts to one part by weight mesna |
| pectin | 0.005-0.04 parts to one part by weight mesna |
| sodium alginate | 0.003-0.01 parts to one part by weight mesna. |

The granulated preferably contains, in addition to the active substance means, lactose, calcium hydrogen phosphate, corn starch and polyvinyl pyrrolidone (as binding agent).

Calcium hydrogen phosphate is used for example as filling agent and the corn starch is preferably used as tablet disintegrant. The outer tablet phase preferably contains corn starch—again as disintegrant—and microcrystalline cellulose (Avicel) as dry binding agent.

The lactose used is preferably a lactose with the following grain size fractions:

| | |
|---|---|
| grain distribution | 100% < 800 µm |
| | 12-35% < 400 µm |
| | maximum 7% < 200 µm |

It is also beneficial if the lactose has the following characteristics:

| | |
|---|---|
| bulk weight: | 560 g/liter |
| tamped weight: | 620 g/liter |
| angle of slope (free-flowing properties) | 35° C. |

The polyvinyl pyrrolidone may for example be the types K 25, K 30 and K 90.

Polyvinyl pyrrolidone are characterized with the K value derived from the relative viscosity. It is a unit reflecting the degree of polymerization and the molecular weight. The previously mentioned polyvinyl pyrrolidones are characterized by the following parameters:

| | |
|---|---|
| Molecular weights: | PVP K 25 = 29,000 |
| | PVP K 30 = 45,000 |
| | PVP K 90 = 1,100,000 |

Grain size distribution in %:

| | >50 µm | >100 µm | >200 µm | >250 µm |
|---|---|---|---|---|
| PVP K 25 | 90% | 50% | 5% | maximum 1% |
| PVP K 30 | 90% | 50% | 5% | maximum 1% |
| PVP K 90 | | | 95% | 90% |

Bulk density:
PVP K 25=400-600 g/liter
PVP K 30=400-600 g/liter
PVP K 90=110-250 g/liter To granulate the active substance mesna, a mixture of isopropanol and water is preferably used containing for example 10% to 50%, preferably 20% to 40% and in particular 30% to 35% water. Related to the active substance mesna, this granulation liquid is for example used to the extent of 0.3 to 3 parts, preferably 0.5 to 2 parts and in particular 0.7 to 1 part. Instead of isopropanol it is also possible to use other $C_1$-$C_4$-alcohols (such as methanol, ethanol) or acetone. These agents, too, may be used as mixtures with water, the same mixing ratios being suitable as for the isopropanol water mixtures. It is also advantageous to add to the granulating solution a binding agent such as polyvinyl pyrrolidone, the amount of polyvinyl pyrrolidone being for example 0.1% to 10%, preferably 1% to 5% and in particular 3% to 5%.

It may in addition also be advantageous to add other conventional pharmaceutical auxiliary substances and carriers to the granulate, or to granulate these together with the other ingredients.

In addition, the tablets may contain anti-adhesion agents, absorption accelerators, hydrophilization agents, moisturizing agents and agents equivalent thereto, as well as conventional flavoring, sweetening and aromatizing agents.

Should the tablet of the invention be an effervescent tablet, it also contains, in addition, a conventional physiologically acceptable effervescent mixture. The amount of this effervescent mixture is 0.05-30 parts by weight for each part by weight of mesna. An effervescent mixture of this type consists of a substance which produces carbon dioxide in the presence of an acid in aqueous or alcoholic medium ($CO_2$ supplier) and a physiologically acceptable organic acid. $CO_2$ supplying substances that may for example be considered are: carbonates or bicarbonates of sodium, potassium, magnesium or calcium; in the case of magnesium and calcium, the neutral carbonates are preferred. Mixtures of these carbonates are also possible. Organic acids which may, for example, be used to liberate carbon dioxide from carbonates of this kind are organically saturated or unsaturated di- and tricarboxylic acids having 2 to 8, preferably 2 to 6 carbon atoms and which may also contain one, two, three or four, preferably one or two hydroxy groups. Examples of such acids are: citric acid, tartaric acid, adipic acid, maleic acid, fumaric acid. Alginic acid may also be used. Mixtures of these acids are also possible.

One part by weight of mesna is for example used with 0.02-18 parts by weight of the $CO_2$-supplying component of the effervescent mixture and 0.03-12 parts by weight of the appropriate acid component. In manufacturing the effervescent tablet it is for example possible to add the entire effervescent mixture as such after the granulating stage. It is, however, also possible and/or preferred to add the components of the effervescent mixture supplying the carbon dioxide before the granulation and then to mix the correspondingly appropriate acid component into the dry granulate later, together with for example the lubricant, the flavoring, sweetening and aromatizing agents as well as optionally the remaining filling and binding agents and disintegrants.

To cover the unpleasant taste of mesna more effectively, it has been found useful to provide a suitable coating for mesna tablets intended for oral administration. This coating may be a conventional sugar coating or also a polymer-containing film coating. It is, for example, possible to use: a copolymerizate of dimethylaminoethyl methacrylate and neutral methacrylic acid esters (for example Eudragit E), hydroxypropyl methylcellulose, molecular weight 11 000 (for example Pharmacoat 606), ethyl cellulose (for example Aquacoat).

The manufacture of the tablets (all steps except for the drying) is for example carried out at temperatures between 10° C. and 80° C., preferably 18° C. to 50° C., in particular 20° C. to 30° C.

Drying of the granulate is for example carried out between 40° C. and 80° C., preferably 50° C. to 70° C.

Should the granulate as such be used as a medicament, for example as a drinkable granulate, this preferably only contains a binding agent in addition to the active substance mesna. The binding agent may be one of the cited binding agents, but it is also possible to use mixtures of such binding agents. It is preferable to use 0.1-1 parts by weight of binding agent for each part by weight of mesna. The maximum grain size of such a granulate is in the region of 3 mm.

The granulate contains for example 100 mg to a maximum of 2 g mesna. The mesna is generally present in the granulate in an amount composing 10–80 percent by weight of the granulate mass. Binding agents, filling agents and optionally lubricants are used in the same order of quantity as in the case of the tablets.

To mask the taste, it is advisable to provide a coating for a granulate which is intended to be taken directly. The coating may be a known and conventional coating which for example only dissolves in acid gastric juice or which may, however, be gastric juice-resistant and only pass into solution in the intestinal tract.

It is also advisable to add flavoring, sweetening and/or aromatizing substances to the granulate.

Aromatizing substances which may for example be considered are: pineapple, apple, apricot, raspberry, cherry, cola, orange, passion fruit, lemon, grapefruit.

The granulate should contain 0.05-0.2 parts by weight of flavoring, related to 1 part by weight of mesna.

The following substances may be used as sweetening agents: saccharine and its sodium salt, cyclamic acid and its sodium salt, ammoniumglycyrrhizinate, fructose, saccharose, xylitol, glucose, sorbitol, mannitol. The granulate should contain 0.003-12 parts by weight of sweetener, related to 1 part by weight of mesna.

To improve the taste, the granulate may be coated with a lacquer that is insoluble in water. The following substances are for example used for this purpose:

Copolymerizates of dimethylamino methacrylic acid and neutral methacrylic acid esters which are insoluble in water and saliva, but which, however, dissolve in an acid medium (such as for example Eudragit[1] E).

It is, however, also possible to use gastric juice-resistant lacquers such as shellac, cellulose acetate phthalate, hydroxypropyl methylcellulose phthalate or polymerizate of methacrylic acid and methacrylic acid esters (for example Eudragit[1] L and S). These gastric juice resistant granulates may be used to stabilize organic acids in order to adjust the applicable suspension to a weakly acid form. The granulate should be coated with 0.0125-2 parts by weight of dry lacquer substance to 1 part by weight of mesna.

The flavoring, sweetening and aromatizing substances cited may also be used in the amounts quoted for the mesna tablets of the invention. The same also applies to the coatings.

DETAILED DESCRIPTION OF PREFERRED EMBODIMENTS

The invention is illustrated by the following examples:

EXAMPLE 1

To prepare a granulate for 4000 tablets containing 300 mg mesna per tablet, 1200 grams mesna, 280 grams lactose, 120 grams calcium hydrogen phosphate and 120 grams corn starch are passed through a sieve of 0.8 mm mesh size and then homogenized for 15 minutes in a suitable mixer. The result is then moistened with a mixture of 616 grams isopropanol and 284 grams water which contains 60 grams polyvinyl pyrrolidone and the moist mass is passed through a sieve of 2 mm pore size.

The granulate is for example dried in a fluidized air bed at an air inlet temperature of 70° C. for a period of 8 minutes.

The dried granulate is then for example passed through a 0.8 mm sieve together with 80 grams corn starch and 120 grams microcrystalline cellulose and homogenized for 20 minutes in a suitable mixer.

Subsequently, 20 grams magnesium stearate are added and mixing is continued for 2 minutes. The mixture so obtained is pressed on a suitable tablet press for example into tablets having the following characteristics:

| | |
|---|---|
| nominal mass | 500.0 mg |
| diameter | 11.0 mm |
| radius of curvature | 8.5 mm |
| thickness | 5.4–5.6 mm |

The tablets may then be continuously sprayed in a suitable apparatus with 225 grams of a film suspension (containing a conventional polymer-containing coating material or a conventional sugar-containing coating material) in such a way that the individual tablet contains a film weighing 15 mg.

EXAMPLE 2

To prepare a mesna granulate, 4 kg of mesna (pure substance) is moistened with 1.9 kg of a solution of 114 grams polyvinyl pyrrolidone having a K value of 25 in a mixture of 1126 grams isopropanol and 660 grams water and passed through a 2 mm sieve. This moist mass is dried in a fluidized air bed to a residual moisture of less than 30% relative humidity and sieved to a maximum grain size of 1 mm. To mask the taste, this granulate is coated in a fluidized air bed apparatus with a suspension having the following composition:

| | |
|---|---|
| Eudragit[1] E (12.5% solution in isopropanol/acetone) | 4.80 kg |
| Magnesium stearate | 0.48 kg |
| Isopropanol | 6.72 kg |
| Total | 12.00 kg |

Eudragit[1] E is a commercially available cationic polymerizate on a methacrylate base for coating pharmaceutical compositions.

It is advisable to carry out an intermediate drying process following the application of 6 kg suspension and to pass the granulate through a 1.5 mm sieve. After application of the entire suspension, sieving is repeated to a grain size of 1.8 mm.

For flavor enhancement, an aromatizing sugar granulate having the following composition is added to this active

| | |
|---|---|
| confectioner's sugar | 14.400 kg |
| flavoring (pulvis) | 0.406 kg |

These components are mixed and moistened with 0.9 kg water, granulated through a 2 mm sieve and dried in a suitable dryer to a residual moisture of less than 30% relative humidity.

Finally, the two granulates are homogenously mixed and filled into pouches in 5 grams batches. Each bag contains 1 gram of mesna.

To ingest, the contents of a bag are suspended in 100 ml water.

What is claimed is:

1. A tablet comprising, as active ingredient, mesna in combination with, for each part by weight of mesna:
   0.01–1 parts by weight of a binding agent selected from the group consisting of polyvinylpyrrolidone, gelatin and microcrystalline cellulose
   0.03–0.4 parts by weight of a disintegrant selected from the group consisting of starch, cross-linked polyvinylpyrrolidone and bentonite
   0.01–0.2 parts by weight of lubricant selected from the group consisting of stearates, talcum and polyglycols
   0.1–1 parts by weight of a filling agent selected from the group consisting of starch, cellulose, lactose, fructose, saccharose, sorbitol, mannitol, calcium phosphate and calcium hydrogen phosphate.

2. A tablet as set forth in claim 1 containing, in addition, at least one member of the group consisting of flavoring, sweetening and aromatizing substances.

3. A tablet according to claim 1 which contains 10–80 percent by weight of mesna.

4. A tablet according to claim 1 which is coated with a pharmaceutically-acceptable film.

5. A process for manufacture of a stable oral dosage form of mesna which contains, for each part by weight of mesna:
   0.01–1 parts by weight of a binding agent selected from the group consisting of polyvinylpyrrolidone, gelatin and microcrystalline cellulose
   0.03–0.4 arts by weight of a disintegrant selected from the group consisting of starch, crosslinked polyvinylpyrrolidone and bentonite
   0.01–0.2 parts by weight of a lubricant selected from the group consisting of stearates, talcum and polyglycols
   0.1–1 parts by weight of a filling agent selected from the group consisting of starch, cellulose, lactose, fructose, saccharose, sorbitol, mannitol, calcium phosphate and calcium hydrogen phosphate said process including the step of granulating the mesna with at least one member of the group consisting of $C_1$–$C_4$-alcohols, acetone and mixtures of these organic agents with water, together with at least a portion of said filling agent and at least a portion of said binding agent, and converting the resulting granulate into a stable oral dosage form of mesna.

6. A process as set forth in claim 5 in which there is present, during the granulation, a disintegrant.

7. A process as set forth in claim 5 including the step of drying the granulate thus formed.

8. A process as set forth in claim 7 including the step of combining the granulate thus formed with a lubricant.

9. A process as set forth in claim 7 or claim 8 including the step of pressing the granulate into tablets.

10. A process as set forth in claim 9 including the step of applying a pharmaceutically-acceptable coating to the tablet.

11. A process for the manufacture of a stable oral dosage form of mesna which consists essentially of, for each part by weight of mesna:
   0.01–1 parts by weight of a binding agent selected from the group consisting of polyvinylpyrrolidone, gelatin and microcrystalline cellulose 0.03–0.4 parts by weight of a disintegrant selected from the group consisting of starch, crosslinked polyvinylpyrrolidone and bentonite 001–0.2 parts by weight of a lubricant selected from the group consisting f stearates, talcum and polyglycols 0.1–1 parts by weight of a filling agent selected from the group consisting of starch, cellulose, lactose, fructose, saccharose, sorbitol, mannitol, calcium phosphate and calcium hydrogen phosphate said process including the step of granulating the mesna with at least one member of the group consisting of $C_1$–$C_4$-alcohols, acetone and mixtures of these organic agents with water, together with at least a portion of said filing agent and at least a portion of said binding agent, and converting the resulting granulate into a stable oral dosage form of mesna.

12. A process as set forth in claim 11 in which there is present, during the granulation, a disintegrant.

13. A process as set forth in claim 11 including the step of drying the granulate thus formed.

14. A process as set forth in claim 13 including the step of combining the granulate thus formed with a lubricant.

15. A process as set forth in claim 13 or claim 14 including the step of pressing the granulate into tablets.

16. A process as set forth in claim 15 including the step of applying a pharmaceutically-acceptable coating to the tablet.

17. A tablet consisting essentially of, as active ingredient, mesna in combination with, for each part by weight of mesna:

0.01–1 parts by weight of a binding agent selected from the group consisting of polyvinylpyrrolidone, gelatin and microcrystalline cellulose 0.03–0.4 parts by weight of a disintegrant selected from the group consisting of starch, cross-linked polyvinylpyrrolidone and bentonite 0.01–0.2 parts by weight of a lubricant selected from the group consisting of stearates, talcum and polyglycols 0.1–1 parts by weight of a filling agent selected from the group consisting of starch, cellulose, lactose, fructose, saccharose, sorbitol, mannitol, calcium phosphate and calcium hydrogen phosphate.

* * * * *